(12) United States Patent
Shinohara et al.

(10) Patent No.: US 8,583,406 B2
(45) Date of Patent: Nov. 12, 2013

(54) VISUAL SIMULATOR FOR SPECTACLE LENS, VISUAL SIMULATION METHOD FOR SPECTACLE LENS, AND COMPUTER READABLE RECORDING MEDIUM RECORDING COMPUTER READABLE VISUAL SIMULATION PROGRAM FOR SPECTACLE LENS

(75) Inventors: Toshihide Shinohara, Chino (JP); Masanori Kakimoto, Hachioji (JP); Tomoaki Tatsukawa, Sagamihara (JP)

(73) Assignee: Hoya Lens Manufacturing Philippines Inc., Cavite (PH)

( * ) Notice: Subject to any disclaimer, the term of this patent is extended or adjusted under 35 U.S.C. 154(b) by 1015 days.

(21) Appl. No.: 12/613,205

(22) Filed: Nov. 5, 2009

(65) Prior Publication Data
US 2010/0114540 A1 May 6, 2010

(30) Foreign Application Priority Data
Nov. 6, 2008 (JP) ................................. 2008-285513

(51) Int. Cl.
*G06F 7/60* (2006.01)
*G06F 7/48* (2006.01)
*G06T 17/00* (2006.01)

(52) U.S. Cl.
USPC .................................. 703/2; 703/6; 345/428

(58) Field of Classification Search
USPC .......................................... 703/2, 6; 345/428
See application file for complete search history.

(56) References Cited

U.S. PATENT DOCUMENTS

| | | | |
|---|---|---|---|
| 6,329,989 B1 * | 12/2001 | Qi et al. | 345/428 |
| 6,517,201 B2 * | 2/2003 | Qi | 351/41 |
| 6,604,826 B2 * | 8/2003 | Akiyama et al. | 351/216 |
| 8,303,113 B2 | 11/2012 | Esser et al. | |

FOREIGN PATENT DOCUMENTS

| | | |
|---|---|---|
| JP | 07333522 A | 12/1995 |
| JP | 11119172 A | 4/1999 |
| JP | 11-183856 | 7/1999 |
| JP | 11338905 A | 12/1999 |
| JP | 2000039564 A | 2/2000 |
| JP | 2005242606 A | 9/2005 |
| JP | 2007-299080 | 11/2007 |
| JP | 2010517085 A | 5/2010 |

OTHER PUBLICATIONS

Masanori Kakimoto et al., "High-Speed Vision Simulation by Front-Tracking Method From Retina" Research Report of Information Processing Society, Information Processing Society of Japan, vol. 2008, No. 9, pp. 7-12, Oct. 31, 2008 (with English abstract).
Japanese language office action dated Jun. 18, 2013 and its English language translation issued in corresponding Japanese application 2009254806.

* cited by examiner

*Primary Examiner* — Kamini S Shah
*Assistant Examiner* — Juan Ochoa
(74) *Attorney, Agent, or Firm* — DLA Piper LLP (US)

(57) ABSTRACT

A visual simulator designs a spectacle lens based on acquired lens design data. Original image data representing an image viewed through the lens and frame data including shape data and layout information of a spectacle frame to which the spectacle lens is fitted are acquired. Image data is generated from the original image data and frame data and displayed on a screen. In an entire display mode, a visual field based on the shape data is entirely displayed on the screen. In a partial display mode, a part of the visual field determined by a distance from the spectacle wearer to the screen and a dimension of the screen is displayed.

6 Claims, 7 Drawing Sheets

VISUAL SIMULATOR FOR SPECTACLE LENS, VISUAL SIMULATION METHOD FOR SPECTACLE LENS, AND COMPUTER READABLE RECORDING MEDIUM RECORDING COMPUTER READABLE VISUAL SIMULATION PROGRAM FOR SPECTACLE LENS

The entire disclosure of Japanese Patent Application No. 2008-285513, filed Nov. 6, 2008 is expressly incorporated by reference herein.

BACKGROUND

1. Technical Field

The present invention relates to a visual simulator, a visual simulation method and a visual simulation program for a spectacle lens to simulate a view through the spectacle lens.

2. Related Art

A typically known simulator simulates a view through a lens such as a spectacle lens on a display area of a display. The view through the lens can be checked beforehand by a simulation image created by the simulator to prevent such a situation that a customer is dissatisfied with a manufactured lens.

Specifically, a simulator that outputs an image corresponding to an actual image that is actually seen through a spectacle lens to a display screen of a CRT and displays a shape of a spectacle frame on the display screen has been suggested (Document 1: JP-A-11-183856 (FIGS. 4 and 5)).

In the simulator disclosed in Document 1, a part of the image outputted within the shape of the spectacle frame is selected and only the selected visual field image is outputted.

Since the shape of the spectacle frame is displayed on the screen according to Document 1, optical performance of the spectacle lens for actual use can be checked on the screen. Especially, the location and degree of the spectacle lens astigmatism and distortion of a progressive power lens after the spectacle lens is fitted into the spectacle frame can be checked on the screen.

However, the size of the display screen of the CRT is typically smaller than a person's visual field. Accordingly, the size of an image viewed through the spectacle lens fitted into the spectacle frame is reduced when being displayed on the display screen. Thus, pixels of an object to be observed are coarse and resolution of the object is reduced, so that the displayed image is more blurred than the actual image. Further, the distortion of the displayed image is different from an actual distortion because of the size reduction.

Though the simulator disclosed in Document 1 can select a part of the image outputted within the shape of the spectacle frame and display the selected part of the image in an enlarged size, it is simply intended to accurately check the image by partially displaying the image in an enlarged size. At this time, the simulator is not intended to check the viewing of the image on the display screen of the CRT actually seen by a spectacle wearer when the spectacle wearer wears the spectacle lens.

An object of the invention is to provide a visual simulator for a spectacle lens, a visual simulation method for a spectacle lens and a visual simulation program for a spectacle lens to experience both of a view through an entire spectacle lens processed into a shape of a spectacle frame and an actual view actually seen by a spectacle wearer.

SUMMARY

According to an aspect of the invention, a visual simulator for a spectacle lens includes: a lens design data acquirer that acquires lens design data on design items of a spectacle lens including a prescription for a spectacle wearer's naked eye; a lens designer that designs the spectacle lens based on the lens design data; an original image data acquirer that acquires original image data to be simulated; a frame data acquirer that acquires frame data including shape data and layout information of a spectacle frame to which the spectacle lens is fitted; an image processor that processes the original image data acquired by the original image data acquirer and generates image data viewed through a lens processed based on the frame data; a display that comprises a screen that displays the image data generated by the image processor; a partial enlargement information acquirer that acquires partial enlargement information of a visual field, the partial enlargement information including a distance from a spectacle lens wearer to the screen of the display and a dimension of the screen, where a processing mode of the image processor includes: an entire display mode in which the visual field based on the shape data is entirely displayed on the screen of the display; and a partial display mode in which a part of the visual field determined by a distance from the spectacle wearer to the screen of the display and the dimension of the screen acquired by the partial enlargement information acquirer.

According to the aspect of the invention, the lens design data acquirer acquires the lens design data on the design items of the lens; the original image data acquirer acquires the original image data to be simulated; the frame data acquirer acquires the shape data and the layout information of the spectacle frame; the partial enlargement information acquirer acquires the partial enlargement information of the visual field including the distance from the spectacle wearer to the screen of the display and the dimension of the screen. Then, the lens designer designs the lens based on the lens design data, and the image processor generates the image viewed through the lens and displays the image on the screen. By setting the entire display mode at this time, optical performance of the spectacle lens for actual use can be checked on the screen that displays the entire shape of the spectacle frame. Depending on the size of the screen of the display, the image that is actually viewed through the spectacle lens is demagnified in the entire display mode. Thus, the partial display mode is set based on the partial enlargement information acquired by the partial enlargement information acquirer according to the aspect of the invention. In the partial display mode, the part of the image corresponding to the visual field determined by the distance from the spectacle wearer to the screen of the display and the screen dimension is displayed on the screen of the display in an enlarged manner, so that the image that is actually viewed through the spectacle lens can be checked in an actual size and thus actual view can be simulated.

Thus, both of the view through the entire lens within the shape of the spectacle frame and the actual view such as blur and distortion through the lens can be experienced.

In the simulator for a spectacle lens according to the aspect of the invention, it is preferable that, the screen of the display is preferably a flat display screen that satisfies the following relationship:

$$\tan(\theta v/2)/\tan(\theta h/2) = Dv/Dh \quad (1)$$

$$L^* \tan(\theta h/2) = K^* Dh \quad (2)$$

where a horizontal dimension of the flat display screen is Dh, a vertical dimension of the flat display screen is Dv, a distance from the spectacle wearer to the flat display screen is L, a horizontal angle of visual field of the image displayed on the flat display screen is θh, a vertical angle of visual field of the image displayed on the flat display screen is θv and K is a constant that satisfies a relationship of 0.35≤K≤0.75.

The formula (1) shows that a horizontal to vertical ratio of the display screen is constant. The formula (2) shows that L*tan(θh/2) is not necessarily equal to Dh and is acceptable as long as L*tan(θh/2) is within a certain range. When K is 0.5, the image to be displayed is equal to the visual field. In other wards, the image has an actual size. When K is smaller than 0.5, the image is magnified. When K is larger than 0.5, the image is dismagnified. The above formulae are deduced to indicate an allowable range in which the image is not largely different from the actual view.

Since the part of the image corresponding to the visual field is accurately determined by the distance from the spectacle wearer to the screen of the display and the screen dimension based on the above formulae, the image can be accurately displayed in the partial display mode.

It is preferable that the image processor includes an enlarged position image generator that generates an enlarged position image indicating a position and a size of an image displayed in the partial display mode within the spectacle frame.

According to the above arrangement, the enlarged position image generator shows the part of the entire display corresponding to the partial display in the partial display mode. Thus, user-friendliness is enhanced when the enlarged position image is displayed with the simulation image.

It is preferable that the image processor receives a signal to switch between the entire display mode and the partial display mode and displays an image in the entire display mode or the partial display mode.

According to the above arrangement, one of the entire display mode and the partial display mode is selectably displayed, so that the visuality of the displayed image is enhanced.

In the visual simulator for a spectacle lens according to the aspect of the invention, the spectacle lens is preferably a progressive lens having a progressive surface.

In the simulator according to the aspect of the invention, the view of the image through the progressive power lens having different views depending on areas of the lens, e.g., a distance part, an intermediate part and a near part corresponding to a distance between the object and the lens can be simulated in a real time manner.

According to another aspect of the invention, a visual simulation method for a spectacle lens includes: acquiring lens design data on design items of a spectacle lens including a prescription for a spectacle wearer's naked eye; acquiring original image data to be simulated; designing the lens based on the lens design data; acquiring frame data including shape data and layout information of the spectacle frame to which the spectacle lens is fitted; processing the original image data acquired by the original image data acquirer to generate image data viewed through a lens processed on the frame data; and displaying the image data generated by the image processor, where the processing switches a processing mode between: an entire display mode in which a visual field of the spectacle frame is entirely displayed on a screen of the display; and a partial display mode in which a part of the visual field determined by a distance from the spectacle wearer to the screen of the display and a dimension of the screen.

According to the another aspect of the invention, the same advantages as described above can be attained.

According to still another aspect of the invention, a computer readable recording medium that stores a visual simulation program for a spectacle lens to execute the simulation method for a spectacle lens as described above in a computer readable manner.

According to the still another aspect of the invention, the spectacle wearer can simulate the view in real time within a short time by the simulation program.

BRIEF DESCRIPTION OF THE DRAWINGS

The invention will be described with reference to the accompanying drawings, wherein like numbers reference like elements.

DESCRIPTION OF EXEMPLARY EMBODIMENT(S)

A visual simulator for a spectacle lens according to an exemplary embodiment of the invention will be described below with reference to the attached drawings.

Arrangement of Visual Simulator for Spectacle Lens

Figure 1:
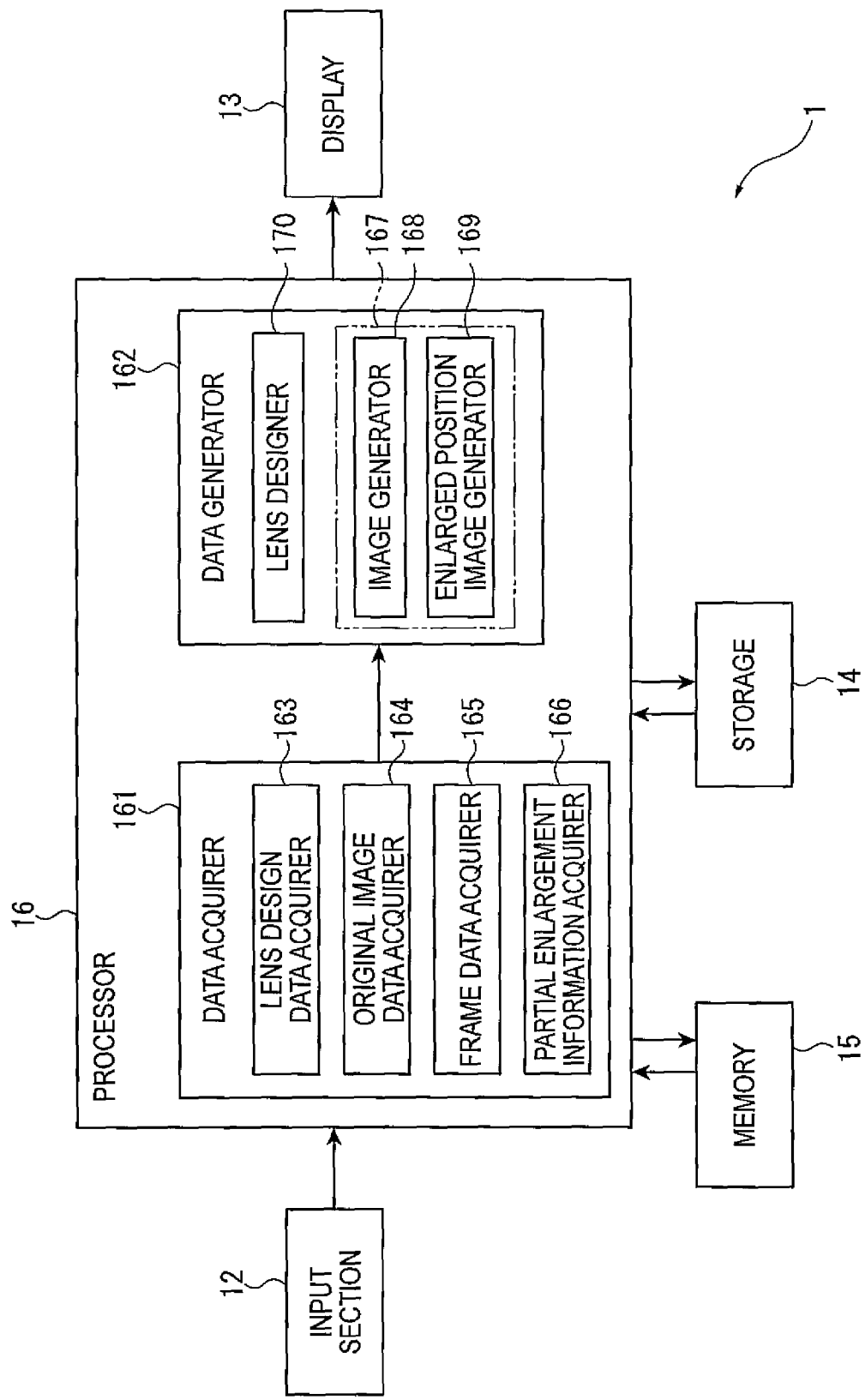
FIG. 1 schematically shows an arrangement of a simulator according to an exemplary embodiment of the invention.

FIG. 1 schematically shows a spectacle lens visual simulator 1 according to an exemplary embodiment.

The spectacle lens visual simulator 1 is placed at, for example, spectacle lens stores.

The spectacle lens visual simulator 1 is exemplified by a personal computer in the exemplary embodiment, but the spectacle lens visual simulator 1 is not limited thereto. The spectacle lens visual simulator 1 may be other arithmetic device such as a portable phone.

As shown in FIG. 1, the visual simulation apparatus 1 for a spectacle lens includes an input unit 12, a display 13, a storage 14 serving as an image recording section, a memory 15, a processor 16.

The input section 12 is a keyboard, a mouse and the like, and has operation buttons or operation knobs (not shown) for an input operation.

Setting items such as movement of the simulator 1 and information to be stored in the simulator 1 are set by the input operation made on the operation buttons or the operation knobs.

In accordance with the input operation for setting, the input section 12 outputs a signal corresponding to the setting to the processor 16 so that the setting is input.

The input operation is not limited to an operation with the operation buttons or the operation knobs. The setting may be input by an input operation on a touch panel provided on the display 13 or by a voice input operation.

Under the control of the processor 16, the display 13 displays a signal of image information inputted from the processor 16 on a display area (not shown). The display 13 includes a display screen 13A having a rectangle shape in plan view and having a horizontal dimension DH and a vertical dimension DV.

The display 13 may be a liquid crystal panel, an organic EL (Electro Luminescence) panel, a PDP (Plasma Display Panel), a CRT (Cathode-Ray Tube), an FED (Field Emission Display), an electrophoretic display panel or the like.

The storage 14 readably stores various data such as customer data, an original image to be simulated, and a shape of a spectacle frame.

The storage 14 may include a drive or a driver that readably stores data in a recording medium such as a HD (Hard Disk), a DVD (Digital Versatile Disc), an optical disc and a memory card.

The customer data relates to a prescription or the like for a lens ordered from a customer who uses the lens. The customer data is provided as one piece of data associated with customer ID (Identification) data, prescription data, lens shape design data and the like.

The prescription data and the lens shape design data provide lens design data of the invention.

The customer ID data is unique information for identifying the customer data, the customer ID data being set for each customer data. The customer data may be a customer number set for each customer, or customer personal information on a customer name and the like.

The prescription data may be data on vision or a lens prescription for the customer of the customer data identified by the customer ID data. The prescription data includes vision data on a vision of a customer, lens prescription data on a prescription for a lens to be designed and the like.

The vision data includes data on the vision of the customer with his naked eyes such as visual acuity, presence of ametropia such as hyperopia, myopia and astigmatism, and accommodation ability. The lens prescription data includes data on a diopter power, an addition power, a spherical power, an astigmatic power, an astigmatic axis, a prismatic power, an inset amount for near vision and the like of a lens.

The lens shape design data is data on a shape of the lens. The lens shape design data includes data on a refractive index or an Abbe number of a lens material, coordinate value data of refracting surfaces (anterior and posterior surfaces) of a lens, thickness data such as a center thickness of the lens, and a design parameter such as progressive length. The lens shape design data may also include data on refraction (such as a refracting power, a prism effect) on points on the lens.

The memory 15 readably stores setting items inputted by the input section 12, audio information, image information and the like. The memory 15 also stores various programs running on an OS (Operating System) operating the whole simulator 1. The memory 15 may include a drive or a driver that readably stores data in a recording medium such as a HD, a DVD, an optical disc and the like.

The processor 16 includes input/output ports (not shown) such as a key input port connected with the input section 12, a display port connected with the display 13, a storage port connected with the storage 14, and a memory port connected with the memory 15.

As shown in FIG. 1, the processor 16 includes a data acquirer 161 and a data generator 162 embodied as programs.

The data acquirer 161 recognizes an input signal generated by an input operation made by a user on the input section 12 and acquires various data based on the input signal. The data acquirer 161 acquires the various data from the storage 14.

The data acquirer 161 includes a lens design data acquirer 163 for acquiring lens design data; an original image data acquirer 164 for acquiring original image data to be simulated; a frame data acquirer 165 for acquiring frame data including data on a shape of a spectacle frame fitted to a spectacle lens and layout information; a partial enlargement information acquirer 166 for acquiring partial enlargement information of a visual field.

The partial enlargement information acquirer 166 acquires the partial enlargement information of the visual field, the partial enlargement information including a distance from a spectacle wearer to a screen of the display 13 and a dimension of the screen. Here, the partial enlargement information includes: the horizontal dimension Dh and the vertical dimension Dv of the display screen 13A; a dimension L between a naked-eye rotation center O of the spectacle wearer and the center of the display screen 13A; and an enlarged position. The dimensions Dh and Dv of the display screen 13A are determined by the display screen of the personal computer, and are inputted via the input section 12 in advance. A distance between the personal computer and the spectacle wearer may be determined in advance and inputted via the input section 12 so as to determine a dimension L between the naked-eye rotation center O of the spectacle wearer and the center of the display screen 13A. Alternatively, a dimension L may be inputted in advance as a given dimension and then the spectacle wearer may sit at a position away from the personal computer by the given diameter. When the screen of the personal computer and an operator are apart by a fixed dimension, for example, 60 cm, the spectacle wearer may sit at a position away from the personal computer by 60 cm.

The enlarged position of the spectacle frame may be set via an operation of the input section 12 (for example, the operation of the mouse) at any one of plurality of positions (for example, a left portion, center portion, or right portion) or may be fixed at, for example, the center portion in advance.

The data generator 162 generates data based on various data acquired by the data acquirer 161.

The data generator 162 includes a lens designer 170 for designing a lens before lens shape machining (design lens) based on lens design data, and an image processor 167 for processing the data acquired by the original image data acquirer 164.

The image processor 167 includes an image generator 168 for showing data of an image viewed through a processed lens provided by the lens shape machining of the design lens, and an enlarged position image generator 169.

The image generator 168 has an entire display mode in which an image corresponding to an entire visual field of a predetermined spectacle frame is displayed on the screen 13A of the display 13, and a partial display mode in which a part corresponding to the visual field determined by the information acquired by the partial enlargement information acquirer 166 is displayed in an enlarged manner. The entire display mode and the partial display mode are switched based on the signal from the input section 12 so that the image is displayed on the display 13 in either one of the modes.

The enlarged position image generator 169 generates an enlarged position image indicating a position and size of a partial image displayed in the partial display mode within the shape of the frame based on the information acquired from the partial enlargement information acquirer 166. The enlarged position image S as described above is displayed at a predetermined position in the simulation image, for example, at a lower and right corner (see FIG. 7).

Operation of Simulator

Figure 2:
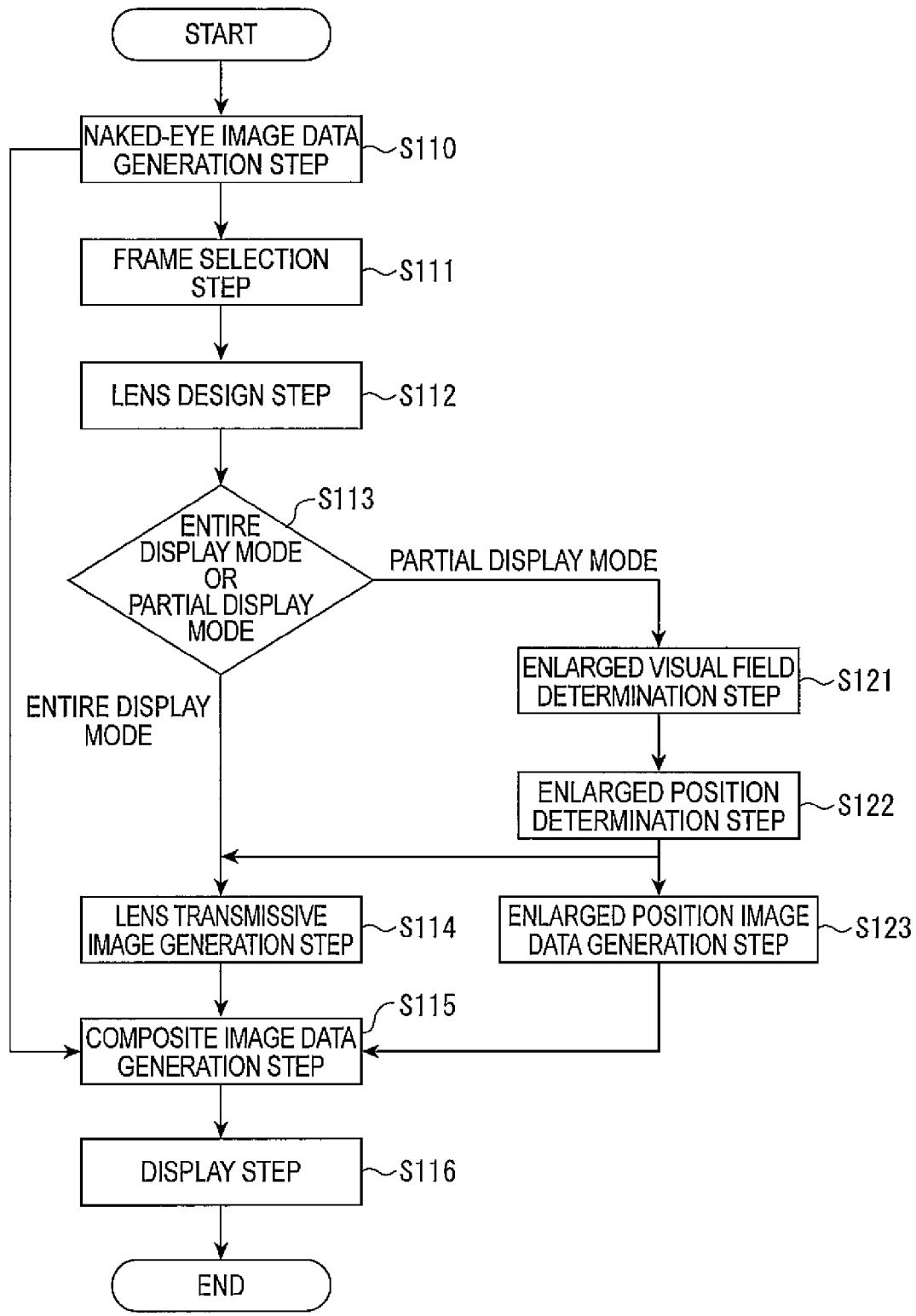
FIG. 2 is a flowchart showing whole operations according to the exemplary embodiment.

Operation of the simulator 1 will be described below with reference to FIG. 2.

Note that the spectacle lens is a progressive lens having a progressive surface in this exemplary embodiment.

Initially, the data generator 162 reads original image to be simulated and visual data of a customer from the storage 14 in a naked-eye image data generation step S110. In this exemplary embodiment, the original image of the exemplary embodiment includes a window and a newspaper in the front to simulate a view through the progressive lens (see FIG. 5). However, the original image is not limited thereto, but may include any landscapes, persons, objects and the like.

Then, the data generator 162 processes the original image to conform to the visual data of the customer, i.e., visual acuity, astigmatism, heterophoria, convergence power and the like.

An image data for a naked eye corresponding to the vision of the customer can be generated, for example, by blurring the contour of the original image, multiplying the contour, blotting the original image, or distorting the original image. The generated naked-eye image data is stored in the storage 14.

In a frame selection step S111, the customer selects a spectacle frame by operating the input section 12 and simultaneously inputs fitting conditions. The frame data acquirer 165 acquires a shape of the selected spectacle frame from the storage 14.

Next, in a lens design step S112, the lens design data acquirer 163 reads lens design data from the storage 14 and the lens designer 170 designs a lens before lens shape machining (design lens) based on the read lens design data.

At this time, the thickness and surface shape of the lens can be adjusted based on the shape of the spectacle frame and the layout information acquired from the frame data acquirer 165.

Then, the image is displayed on the display 13 via an image processing step. To perform the image processing step, the input section 12 initially selects the entire display mode or partial display mode and the image generator 168 receives a select signal corresponding to the selected mode (S113).

For example, when the "entire display mode" is selected, a lens transmissive image generation step S114 to a display step S116 are executed.

In the lens transmissive image generation step S114, the view of the original image through the lens within the shape of the frame selected in the frame selection step S111 is calculated by ray trace or the like to generate lens transmissive image data.

Next, a composite image data generation step S115 is executed. In the composite image data generation step S115, the shape of the frame is plotted in the naked-eye image data and the lens transmissive image is placed within the shape of the frame so as to generate a composite image by combining the naked-eye image outside the frame and the lens transmissive image inside the frame. Then, the composite image is displayed on the screen 13A of the display 13 in the display step S116 (see FIG. 6).

When the "partial display mode" is selected in the step S113, an enlarged visual field determination step 121 is executed. In the enlarged visual field determination step 121, a visual field is determined based on the information acquired by the partial enlargement information acquirer 166. Procedure of determining a visual field will be described below with reference to FIGS. 3 and 4.

Figure 3:
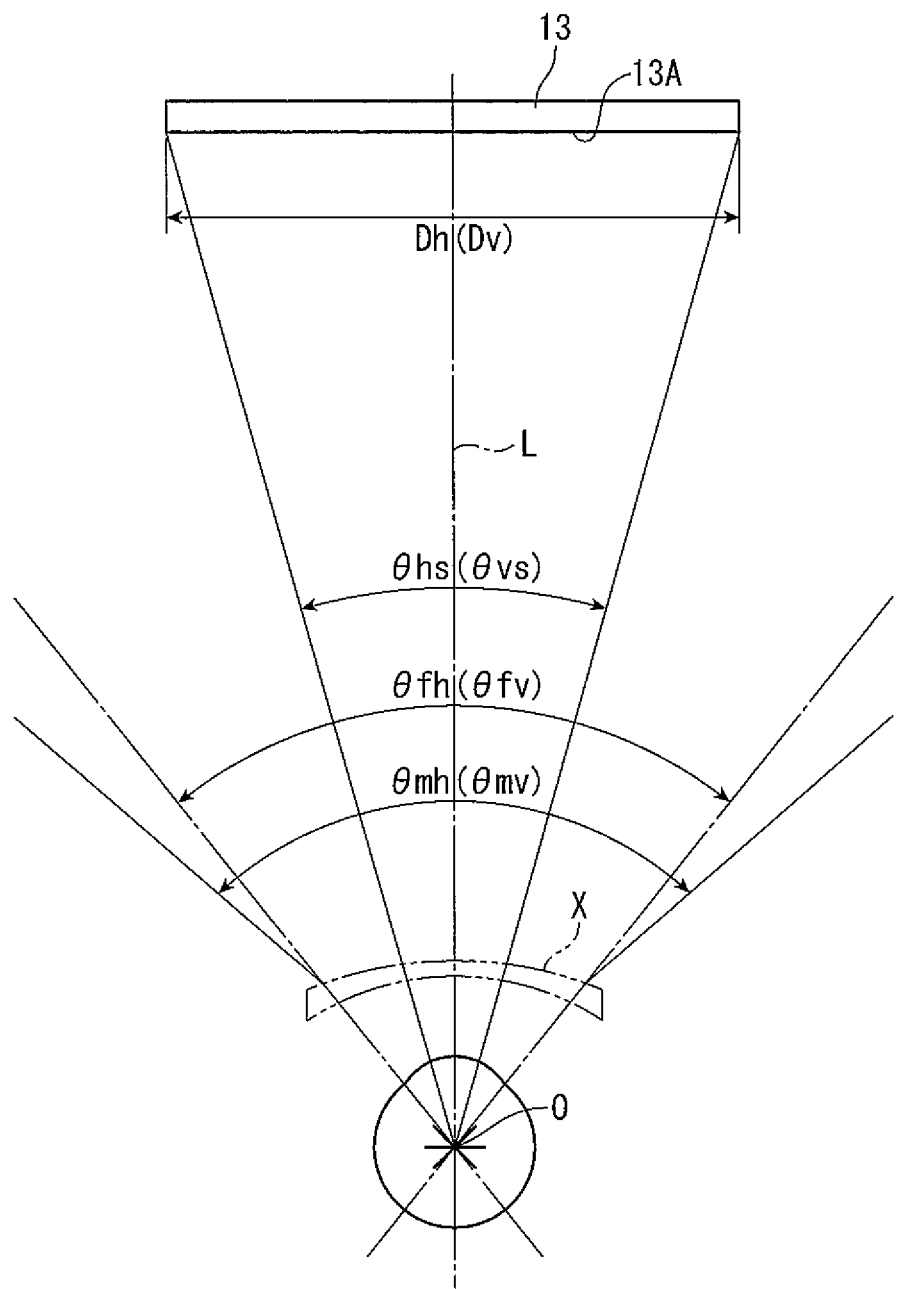
FIG. 3 schematically shows a relationship between a distance from the spectacle wearer to a screen of a display and a visual field.

FIG. 3 shows a horizontal relationship between a distance from the spectacle wearer to the screen of the display 13 and a dimension of the screen. In FIG. 3, a dimension between an eye-ball rotation center O of the spectacle wearer and the center of the flat display screen 13A is denoted as L. A horizontal angle of the visual field corresponding to the flat display screen 13A is denoted as θhs and a vertical angle of the visual field is denoted as θvs. Further, the horizontal angle of visual field corresponding to the partial image displayed on the flat display screen 13A is θh and vertical angle of the visual field is θv. Except for unique screens such as a spherical screen that covers an entire visual field of the spectacle wearer, a horizontal angle of visual field θfh of the spectacle frame is larger than the vertical angle of visual field θhs of the display screen. Similarly, a vertical angle of visual field θfv of the spectacle frame is larger than a horizontal angle of visual field θvs of the display screen.

By refraction of the lens fitted into the frame, a displayable range angle θmh (θmv) seen through a minus lens is larger than the visual field θfh (θfv) of the shape of the frame as shown in FIG. 3, and a displayable range angle θmh (θmv) seen through a plus lens is smaller than the visual field θfh (θfv). An image displayed on the screen in the entire frame when a spectacle wearer wears a spectacle lens X is more dismagnified than an image that is actually seen through the spectacle lens, irrespective of a little magnification or dismagnification of the image by refraction of the lenses.

Here, an aspect ratio of the flat display screen 13A is the same as a ratio of the horizontal screen visual field θh and the vertical screen visual field θv of the partial image displayed on the flat display screen 13A. Thus, the following formula (1) can be deduced. Further, in order to naturally display the partial image as compared to an actual object, the following formulae (2) and (3) are deduced.

$$\tan(\theta v/2)/\tan(\theta h/2) = Dv/Dh \quad (1)$$

$$L^*\tan(\theta h/2) = K^*Dh \quad (2)$$

$$L^*\tan(\theta v/2) = K^*Dv \quad (3)$$

In the formulae (2) and (3), K is a constant. In the exemplary embodiment, K satisfies the relationship of $0.35 \leq K \leq 0.75$ in order for the image displayed when the spectacle lens X is worn to be substantially the same as the image actually seen through the spectacle lens. Especially, K is most preferably equal to 0.5 so that the image displayed when the spectacle lens X is worn is physically the same as the image actually viewed through the spectacle lens. A predetermined value is inputted as the constant K via the input section 12.

In the exemplary embodiment, the visual field θh and the distance L are set to satisfy the formulae (1) and (2), or the visual field θv and the distance L are set to satisfy the formulae (1) and (3). When the distance L is set in advance, the visual field θh (θv) is consequently determined. Incidentally, when K is not equal to 0.5, the partial image is magnified or dismagnified to be in conformity with the size of the display screen 13A.

Figure 4:
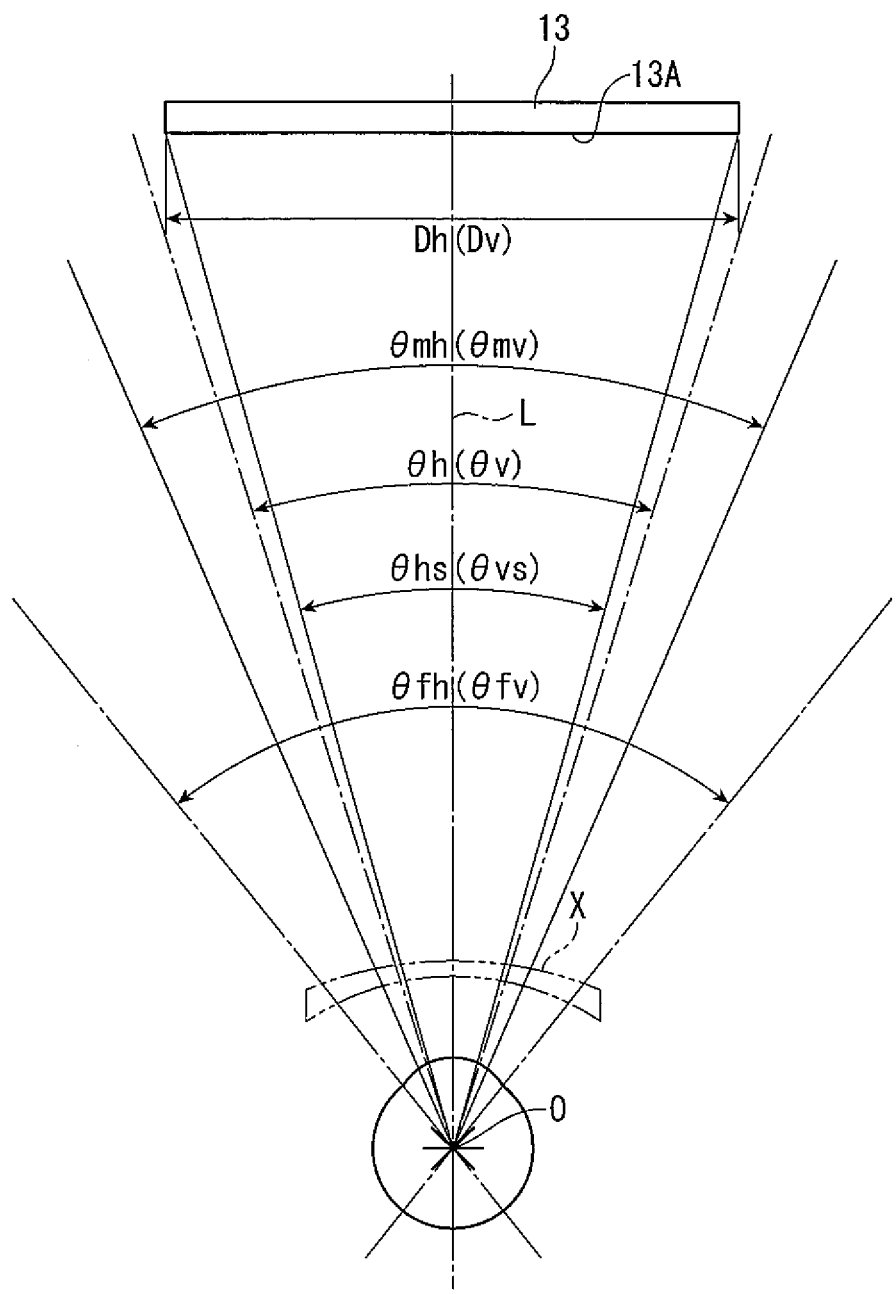
FIG. 4 schematically shows a relationship between the distance from the spectacle wearer to the screen of the display and the visual field.

Thus, resolution of the display screen is enhanced when the displayable range angle θmh (θmv) approaches the visual field θhs (θvs) of the display screen as shown in FIG. 4.

Then, the enlarged position determination step S122 is executed. In the enlarged position determination step S122, a part of the spectacle lens to be enlarged, for example, a center part of the spectacle lens, is set by input operation made on the input section 12.

When the part of the spectacle lens to be enlarged is determined, an image in which the part is enlarged is generated in S114 while the enlarged position image generation step S123 is executed to generate an enlarged position image.

Figure 7:
FIG. 7 shows the simulation image in a partially enlarged manner.

In the enlarged position image generation step S123, an image in which a part P of the spectacle lens to be enlarged within a spectacle frame F is displayed as a square is generated (see FIG. 7).

Then, in the composite image data generation step S115, the image generated in the enlarged position image generation step S123 and the simulation image in which the part of the spectacle lens generated in the step S114 is enlarged are combined as one composite image. The composite image is then displayed on the screen 13A in the display step S116. The added image is displayed as an enlarged position image at a lower and right corner of the simulation image (see FIG. 7).

Advantages of Exemplary Embodiment

According to the exemplary embodiment, the following advantages can be attained.

(1) The spectacle lens visual simulator 1 includes: the image processor 167 for generating the image data that is viewed through the lens by the simulation on the original image data acquired by the original image data acquirer 164; the display 13 having the screen 13A that displays the processed image data generated by the image processor 167; and the partial enlargement information acquirer 166 for acquiring the partial enlargement information of the visual field including the distance L from the spectacle wearer to the screen 13A of the display and the screen dimensions Dh and Dv. The image processor 167 has: the entire display mode in which the entire visual field of the spectacle frame is displayed on the screen 13A; and a partial display mode in which the part of the visual field determined by the distance L from the spectacle wearer to the screen 13A of the display 13, the screen dimensions Dh and Dv acquired by the partial enlargement information acquirer 166 and the constant K. Thus, in the entire display mode, optical performance of the entire spectacle lens for actual use, especially distribution of blur and distortion of an entire progressive power lens, can be checked on the screen that displays the entire spectacle frame. However, the image actually viewed through the spectacle frame is dismagnified to be displayed in the entire display mode. Conversely, in the partial display mode, the image of every part actually viewed through the spectacle lens can be checked in its full size on the partially enlarged display on the screen 13A. On the partially enlarged display, reduction in resolution of objects to be observed because of the dismagnification in the entire display mode can be sufficiently restrained, and the distortion of the image is not varied. Accordingly, the actual blur and distortion of each part of the objects can be experienced.

Thus, both the view through the entire lens fitted into the spectacle frame and the actual view of each part when the spectacle lens is worn can be experienced.

(2) When the horizontal dimension of the flat display screen 13A of the display 13 is denoted as Dh; the vertical dimension is denoted as Dv; the horizontal angle of visual field corresponding to the partial image displayed on the flat display screen 13A is denoted as θh; and the vertical angle of visual field is denoted as θv, the following formulae (1) and (2) can be deduced.

$$\tan(\theta v/2)/\tan(\theta h/2) = Dv/Dh \quad (1)$$

$$L * \tan(\theta h/2) = K * Dh \quad (2)$$

In the above formulae, K is a constant that satisfies the relationship of $0.35 \leq K \leq 0.75$. Thus, the screen display in the partial display mode can be substantially accurately conducted.

(3) Since the image processor 167 includes the enlarged position image generator 169 that generates the enlarged position image S indicating a part of the image displayed in the entire display mode corresponding to a part displayed in the partial display mode, the part of the image in the entire display mode that is displayed in the partial display mode can be checked by the enlarged position image generator 169. Thus, user-friendliness is enhanced by displaying the enlarged position image S with the simulation image.

(4) Since the enlarged position image S generated by the enlarged position image generator 169 is displayed on the corner of the simulation image displayed in the partial display mode, the enlarged position image S does not interfere with the simulation image, thereby enhancing the visuality of the simulation image.

(5) Since the enlarged position image S includes the part P as a square within the spectacle frame F, the image itself is simplified and easily viewable.

(6) Since the image processor 167 receives a signal to switch between the entire display mode and the partial display mode to selectively display the image on the display 13 in either of the modes, the entire display mode and the partial display mode are not mixed when the image is displayed, thereby enhancing the visuality of the displayed image.

(7) Since the spectacle lens is a progressive power lens, the view of the image through the progressive power lens having different views depending on areas of the lens, e.g., a distance part, an intermediate part and a near part corresponding to a distance between the object and the lens can be simulated in a real time manner.

EXAMPLE(S)

Example(s) of the simulation image will be described below with reference to FIGS. 5 and 7.

In the Example, a person's visual field is 60° at its inner side, 95° at its outer side, 60° at its upper side and 70° at its lower side. A horizontal angle of visual field is 155° and a vertical angle of visual field is 130°. A personal computer used as the display 13 has the screen 13A of 14 inch (Dh of 285 mm, Dv of 213 mm), the distance L from the screen to the spectacle wearer of 400 to 500 mm, the horizontal angle θhs of visual field of 39° to 32° and the vertical angle θvs of visual field of 30° to 24°. The spectacle frame has a width of 55 mm, a length of 32 mm, and the distance from a naked-eye rotation center of 25 mm, a horizontal angle of visual field θfh of 98° and a vertical angle of visual field θfv of 65°. As the spectacle lens, a progressive power lens (prescription diopter: S-2.00 (D) Add 2.00(D)) conditioned by an myopia prescription at a distant part.

Figure 5:
FIG. 5 shows a screen to be displayed corresponding to the visual field of a spectacle frame.

FIG. 5 shows a screen to be displayed corresponding to the visual field θfh (θfv) of the spectacle frame. As shown in FIG. 5, the display of the image viewed through the spectacle frame has a wide range.

The visual simulation is desirably displayed by a display on the same condition as the person's visual field. However, such a display has not been widely available because of its size, cost and resolution even if the display has been developed. Thus, it is desirable that the image is displayed on a screen of a commonly available personal computer.

Since the display screen 13A of the personal computer has a horizontal angle of visual field θhs of 50° to 35°, a horizontal angle of visual field is ⅓ to ¼ of the spectacle wearer's horizontal angle of visual field of 155°.

When the image is viewed at a position that is approximately 40 cm away from the display screen 13A of the personal computer having 14 inch, a horizontal angle of visual field θhs of the display screen 13A is approximately 40°.

Figure 6:
FIG. 6 shows a simulation image of the entire spectacle frame.

FIG. 6 shows the simulation image in the entire spectacle frame displayed on the screen 13A of the display 13 in the entire display mode. In FIG. 6, the spectacle frame F is displayed fully over the frame of the flat display screen 13A, so that the optical performance of the whole spectacle lens for actual use can be checked on the screen entirely displayed in the spectacle frame F. When the aspect ratio of the frame is not coincident to the aspect ratio of the display screen 13A in the entire display mode of the spectacle frame, the display size is adjusted so that the entire frame falls in the screen while keeping the aspect ratio of the visual field of the frame. Incidentally, in FIG. 6, blurring from the intermediate part to the near part, which is characteristics of the progressive power lens, is displayed in a faded state.

Since the horizontal angle of visual field $\theta fh$ of the spectacle frame is 98° while the horizontal angle of visual field $\theta hs$ of the display screen 13A is 40° shown in FIG. 6, the image shown in FIG. 6 is zoomed by approximately 40%. Accordingly, the image shown in FIG. 6 has lower definition and the blurring through the spectacle lens, which is intended to be simulated, is not accurately displayed. Specifically, the displayed characters and the like are smaller than an actual characters and the like in all of the distance part E1, intermediate part E2 and near part E3, so that the resolution is lowered.

FIG. 7 shows the simulation image that is partially enlarged in the partial display mode to be displayed on the display screen 13A. The enlarged position image S generated in the enlarged position image generation step S123 is also displayed at the lower right corner of the display screen 13A. In the enlarged position image S, the spectacle frame F is schematically displayed inside a frame S1 having a rectangular shape. The part P of the spectacle lens to be enlarged is displayed as a square in the spectacle frame F.

In FIG. 7, the displayable range angle $\theta mh$ ($\theta mv$) is close to the visual field $\theta hs$ ($\theta vs$) of the display screen 13A. As compared to FIG. 6, the letters are displayed in a large size and the blurring is reduced, so that the image is clear.

In Example, K that satisfies the formulae (1) and (2) satisfies the relationship of $0.35 \leq K \leq 0.75$.

The displayable range angle $\theta mh$ is 55° that is close to the horizontal angle of visual field $\theta hs$ of the display screen 13A of 40°. In other words, the image is zoomed by approximately 73%. The view of the displayed image is approximately the same as the actual view.

By using the two display modes, the view through the spectacle lens can be accurately checked in an apparatus including the display 13 having the display screen 13A of a typical size.

Modifications of Exemplary Embodiment

The invention is not limited to the exemplary embodiment, but includes below-described modifications and the like as long as an object of the invention can be achieved.

For example, though the blurring from the intermediate part to the near part of the progressive power lens is displayed in a faded state, the blurring is not necessarily displayed.

Further, the simulation image generated in the entire display mode and the simulation image generated in the partial display mode may be adjacently displayed on the display screen 13A by the image processor 167. The display screen 13A is not limited to the rectangular shape in plan view, but may have other shape such as a circular shape and triangular shape.

The invention is not limited to the simulator 1 as described in the above exemplary embodiment, but may be provided by a simulation program operating an arithmetic unit such as a computer as the simulator 1 and a recording medium such as a CD-ROM and a memory card recording the simulation program in a manner readable by the arithmetic unit.

In addition, a specific structure and procedure when carrying out the invention can be changed to another structure and the like without departing from an object of the invention.

What is claimed is:

1. A visual simulator for a spectacle lens comprising:
a lens design data acquirer that acquires lens design data on design items of a spectacle lens including a prescription for a spectacle wearer's naked eye;
a lens designer that designs the spectacle lens based on the lens design data;
an original image data acquirer that acquires an original image data;
a frame data acquirer that acquires frame data including shape data and layout information of a spectacle frame to which the spectacle lens is fitted;
an image processor that processes the original image data acquired by the original image data acquirer and generates image data representing an image viewed through a lens processed based on the frame data;
a display that comprises a screen that visually simulates by displaying the image based on the image data generated by the image processor;
a partial enlargement information acquirer that acquires partial enlargement information of a visual field, the partial enlargement information including a distance from a spectacle lens wearer to the screen of the display and a dimension of the screen, wherein
a processing mode of the image processor includes: an entire display mode in which the visual field based on the shape data is entirely displayed on the screen of the display; and a partial display mode in which a part of the visual field determined by the distance from the spectacle wearer to the screen of the display and the dimension of the screen acquired by the partial enlargement information acquirer is displayed,
the screen of the display is a flat display screen that satisfies the following relationship:

$$\tan(\theta v/2)/\tan(\theta h/2) = Dv/Dh \quad (1)$$

$$L*\tan(\theta h/2) = K*Dh \quad (2)$$

where a horizontal dimension of the flat display screen is Dh, a vertical dimension of the flat display screen is Dv, a distance from the spectacle wearer to the flat display screen is L, a horizontal angle of the visual field corresponding to the image displayed on the flat display screen is $\theta h$, a vertical angle of the visual field corresponding to the image displayed on the flat display screen is $\theta v$ and K is a constant that satisfies a relationship of $0.35 \leq K \leq 0.75$.

2. The visual simulator for a spectacle lens according to claim 1, wherein the image processor includes an enlarged position image generator that generates an enlarged position image indicating a position and a size of the image displayed in the partial display mode within the spectacle frame.

3. The visual simulator for a spectacle lens according to claim 1, wherein the image processor receives a signal to switch between the entire display mode and the partial display mode and displays an image in the entire display mode or the partial display mode.

4. The visual simulator for a spectacle lens according to claim 1, wherein the spectacle lens is a progressive lens having a progressive surface.

5. A visual simulation method for a spectacle lens comprising:
acquiring lens design data on design items of a spectacle lens including a prescription for a naked eye of a spectacle wearer;

acquiring original image data;
designing the lens based on the lens design data;
acquiring frame data including shape data and layout information of a spectacle frame to which the spectacle lens is fitted;
processing the acquired original image data to generate image data viewed through a lens processed on the frame data; and
displaying the generated image data, wherein
in the displaying, the image data is visually simulated by displaying on a flat display screen,
the processing switches a processing mode between: an entire display mode in which a visual field of the spectacle frame is entirely displayed on the flat display screen; and a partial display mode in which a part of the visual field determined by a distance from the spectacle wearer to the flat display screen and a dimension of the flat display screen is displayed, and
the flat display screen satisfies the following relationship:

$$\tan(\theta v/2)/\tan(\theta h/2) = Dv/Dh \tag{1}$$

$$L*\tan(\theta h/2) = K*Dh \tag{2}$$

where a horizontal dimension of the flat display screen is Dh, a vertical dimension of the flat display screen is Dv, a distance from the spectacle wearer to the flat display screen is L, a horizontal angle of the visual field corresponding to the image displayed on the flat display screen is θh, a vertical angle of the visual field corresponding to the image displayed on the flat display screen is θv and K is a constant that satisfies a relationship of $0.35 \leq K \leq 0.75$.

6. A non-transitory computer readable recording medium storing computer executable instructions that when executed by a processor perform all steps of claim 5.

* * * * *

UNITED STATES PATENT AND TRADEMARK OFFICE
CERTIFICATE OF CORRECTION

| | |
|---|---|
| PATENT NO. | : 8,583,406 B2 |
| APPLICATION NO. | : 12/613205 |
| DATED | : November 12, 2013 |
| INVENTOR(S) | : Toshihide Shinohara et al. |

Page 1 of 1

It is certified that error appears in the above-identified patent and that said Letters Patent is hereby corrected as shown below:

On the title page, item (73), column 1, please add the assignee "SGI JAPAN, LTD., Tokyo (JP)"

Signed and Sealed this
Fifteenth Day of April, 2014

Michelle K. Lee
*Deputy Director of the United States Patent and Trademark Office*